US006575976B2

(12) United States Patent
Grafton

(10) Patent No.: US 6,575,976 B2
(45) Date of Patent: Jun. 10, 2003

(54) EXPANDABLE TISSUE ANCHOR

(75) Inventor: R. Donald Grafton, Naples, FL (US)

(73) Assignee: Arthrex, Inc., Naples, FL (US)

( * ) Notice: Subject to any disclaimer, the term of this patent is extended or adjusted under 35 U.S.C. 154(b) by 9 days.

(21) Appl. No.: 09/878,192

(22) Filed: Jun. 12, 2001

(65) Prior Publication Data

US 2001/0051807 A1 Dec. 13, 2001

Related U.S. Application Data

(60) Provisional application No. 60/210,830, filed on Jun. 12, 2000.

(51) Int. Cl.[7] .............................................. A61B 17/56
(52) U.S. Cl. .............................. 606/72; 606/67; 606/68
(58) Field of Search ............................ 606/65, 67, 68, 606/72, 75, 151

(56) References Cited

U.S. PATENT DOCUMENTS

| 4,871,289 A | 10/1989 | Choiniere | 411/48 |
| 5,268,001 A | 12/1993 | Nicholson et al. | 606/72 |
| 5,336,240 A | 8/1994 | Metzler et al. | 606/232 |
| 5,601,558 A * | 2/1997 | Torrie et al. | 606/72 |
| 5,713,903 A * | 2/1998 | Sander et al. | 606/72 |
| 5,968,044 A | 10/1999 | Nicholson et al. | 606/72 |

OTHER PUBLICATIONS

Advertisement from Mitek for "CuffTack—Sutureless Fixation Device", Mitek Products, Division of ETHICON, Inc., Feb. 2001.

* cited by examiner

Primary Examiner—Gregory L. Huson
Assistant Examiner—Lina R Kontos
(74) Attorney, Agent, or Firm—Dickstein Shapiro Morin & Oshinsky, LLP

(57) ABSTRACT

A bioabsorbable, cannulated expandable tissue anchor for sutureless soft tissue fixation to bone, particularly in arthroscopic shoulder surgery. The anchor is provided with a ribbed shaft and a head for securing the soft tissue to bone. The shaft of the anchor is divided into at least two legs by longitudinal slots which extend from the distal end of the anchor. After the anchor is installed through tissue and into bone, a dowel is inserted into the proximal end of the cannulated shaft to axially spread apart the legs of the shaft by opening the longitudinal slots, thereby securing the anchor in the bone.

15 Claims, 3 Drawing Sheets

EXPANDABLE TISSUE ANCHOR

This application claims the benefit of U.S. Provisional Application Ser. No. 60/210,830, filed Jun. 12, 2000.

BACKGROUND OF THE INVENTION

1. Field of the Invention

The present invention relates to an expandable tissue anchor, and more specifically, to an expandable, biodegradable tissue anchor for use in arthroscopic surgical shoulder repair.

2. Description of the Related Art

Expandable anchors are known for use in surgical applications. Examples include U.S. Pat. Nos. 5,268,001 and 5,968,044 to Nicholson et al., which disclose a bone fastener having an expandable sleeve with an axial bore, and a pin with an outer diameter greater than an inner diameter of at least a portion of the axial bore for expanding the sleeve. A holder is severably attached to the sleeve for use during installation. U.S. Pat. No. 5,336,240 to Metzler et al. discloses an expandable anchor in which a pin is pulled proximally to deploy the device.

Other expandable anchors are known for anchoring to building materials such as brick and concrete. For example, U.S. Pat. No. 4,871,289 to Choiniere discloses an expandable anchor with an expanding pin. The pin has a radial shoulder such that the pin locks inside the expandable anchor sleeve after insertion and expansion.

All of these prior art devices require a pre-drilled hole for installation of the anchor. The anchor is placed into the pre-drilled hole and then expanded to provide fixation.

Accordingly, a need exists in the prior art for an expandable anchor that does not require pre-drilling of a bore that accommodates the anchor.

SUMMARY OF THE INVENTION

The present invention provides an expandable anchor that is driven into bone without the need for pre-drilling a bore to accommodate the anchor. The anchor utilizes an inner dowel pin, preferably made of a bioabsorbable material such as PLLA, to expand the anchor after it is pushed into place in the bone, and to hold the pin within the anchor. During insertion, the spreadable tip of the anchor is held together by a frangible connection formed of a non-slotted section at the tip of the anchor. As the dowel pin is advanced and the anchor legs spread, the connections are severed to allow complete expansion. In certain types of bone, it may be necessary to punch or drill a small hole to receive the tip of the anchor. Typically, however, no pre-drilling of bone is required.

Advantageously, the non-slotted section allows for driving the device into hard bone without prematurely expanding. Preferably, the push in dowel is made up of low molecular weight polymer to expand in a short period to fixate the dowel as well as increase the overall expansion of the device. In addition, the head is radiused to contour with the anatomical shape of the soft tissue and underlying bone.

Other features and advantages of the present invention will become apparent from the following description of the invention which refers to the accompanying drawings.

DETAILED DESCRIPTION OF THE PREFERRED EMBODIMENTS

Figure 1:
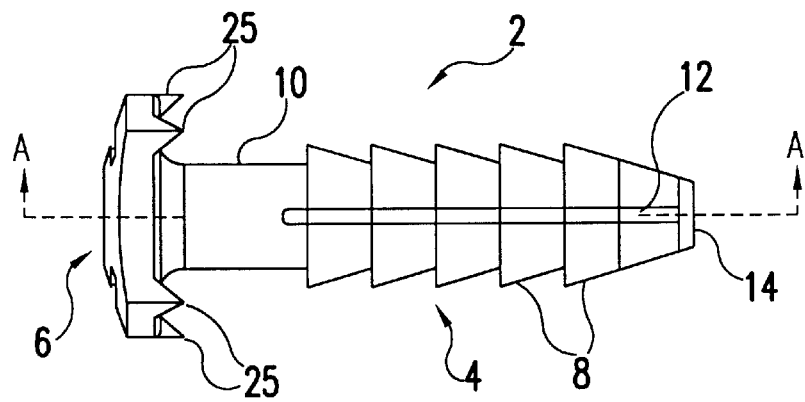
FIG. 1 is an elevation of an expandable tissue anchor according to the present invention.

Referring to FIG. 1, an expandable, bioabsorbable tissue anchor 2 according to the present invention is shown. Tissue anchor 2 has a body 4 and a head 6. The body 4 includes a series of ridges 8 for engaging bone. The body 4 includes a smooth shank 10 attached to the head 6. The ridged portion of body 4 is divided into two legs by a pair of slots 12. A non-slotted portion 14 at the distal end of the body 4 connects the two legs together to prevent them from expanding prematurely during insertion of the anchor, as described further below.

Figure 2:
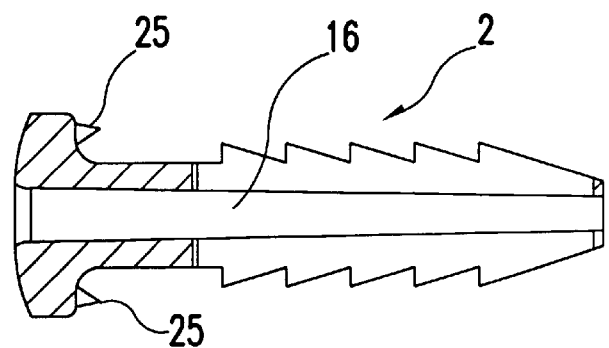
FIG. 2 is a cross-sectional plan view of the expandable tissue anchor taken along the line A—A of FIG. 1.
Figure 3:
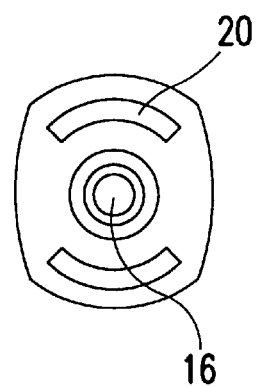
FIG. 3 is a top end view of the tissue anchor of FIG. 1.
Figure 6:
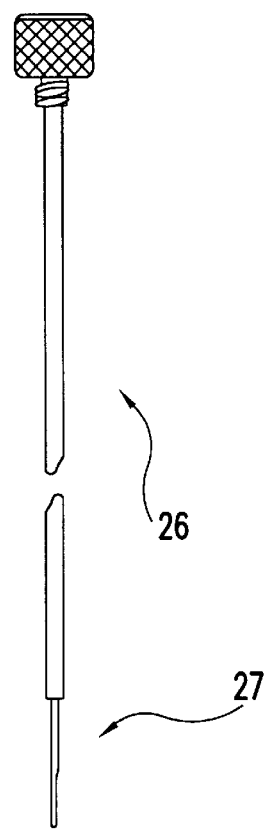
FIG. 6 illustrates an anchor insertion assembly according to the present invention.
Figure 4:
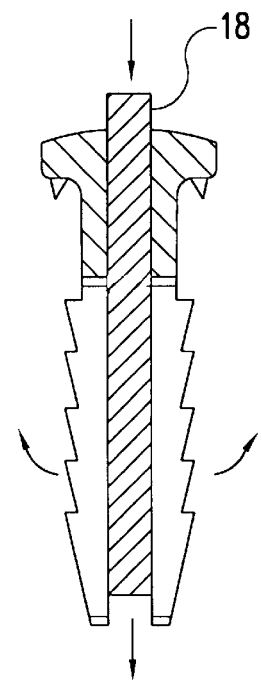
FIG. 4 illustrates the tissue anchor with the dowel pin being inserted into the anchor.

Referring to FIGS. 2 and 3, the anchor 2 has a cannula 16 formed along its length. The cannula tapers at least toward the distal end to form a narrower opening. A straight dowel pin 18, shown in FIG. 4, is inserted into the cannula and expands the anchor by forcing apart the legs of the anchor. As the dowel pin is advanced, the non-slotted portion 14 initially prevents the legs from spreading at the distal tip, and subsequently severs under the increased tension provided by the advancing dowel, thereby allowing the legs to spread apart freely.

Figure 5:
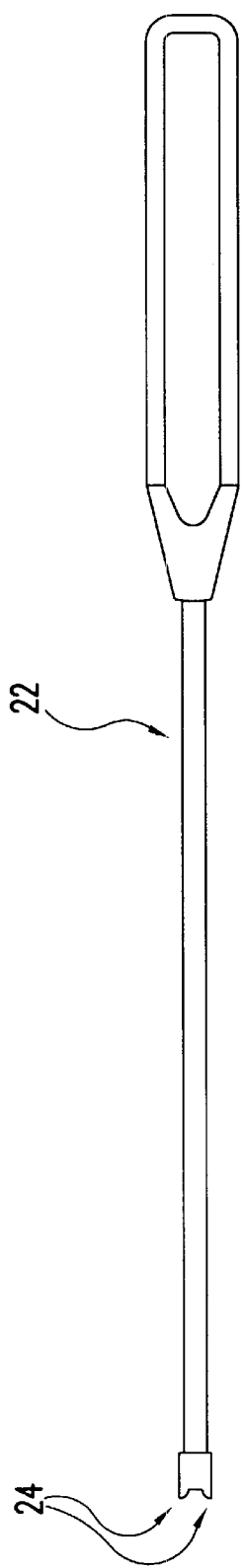
FIG. 5 illustrates a driver for the tissue anchor according to the present invention.

The head 6 of the anchor is provided with a pair of slots 20 that accept a driver 22 shown in FIG. 5. The distal end of the driver features a pair of cleats 24 that correspondingly engage the slots 20 on anchor head 6. The head 6 is radiused anatomically. Six barbs 25 are provided around the head 6 to enhance the purchase on tissue.

According to a preferred method of fixating tissue according to the present invention, an anchor insertion assembly 26 is inserted into driver 22. The anchor 2 is placed on the distal end of the driver 22, over the tapered portion 27 of the anchor insertion assembly 26, which protrudes from the distal end of driver 22. Approximately 5 mm of the distal tip of anchor insertion assembly 26 extends beyond the distal tip of the anchor to provide a sharp point for penetrating tissue and bone. The pointed distal tip of the anchor insertion assembly is placed against the tissue to be fixated, the tissue is approximated adjacent the bone attachment site, and the anchor is driven into the bone by impaction, for example. If necessary, a punch or drill can be used initially to penetrate the tissue and/or the cortical layer of bone prior to insertion of the anchor using the anchor insertion assembly and the anchor driver.

Figure 9:
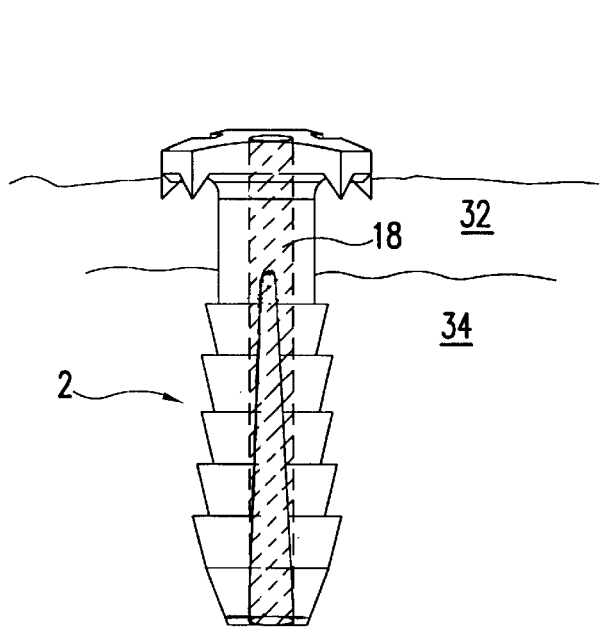
FIG. 9 illustrates the tissue anchor of the present invention inserted through tissue and into bone, with dowel pin inserted.
Figure 7:
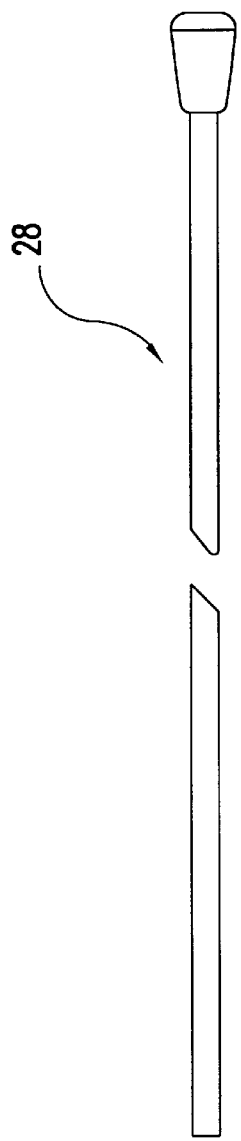
FIG. 7 illustrates a dowel pin insertion assembly according to the present invention.
Figure 8:
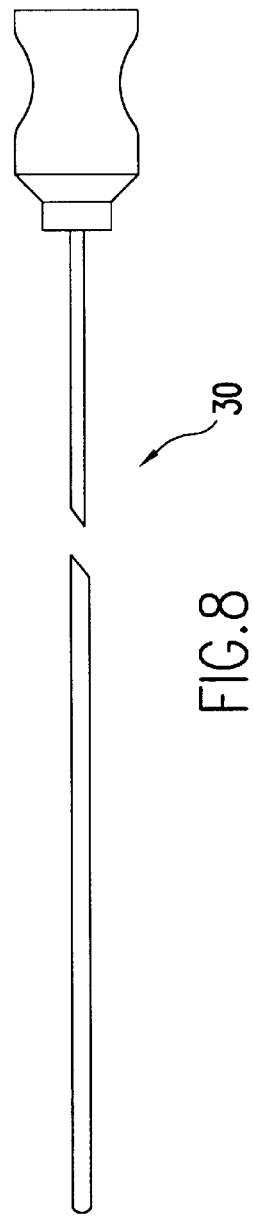
FIG. 8 illustrates a dowel pin driver assembly according to the present invention.

Once the anchor has been driven into the bone, anchor insertion assembly 26 is removed from the driver 22, and is replaced by a cannulated pin insertion assembly 28 shown in FIG. 7. The dowel pin 18 is inserted into the pin insertion assembly and advanced using pin driver 30 shown in FIG. 8. The pin driver 30 is used to advance the dowel pin inside the tissue anchor to expand the anchor as described above. The pin driver assembly engages the proximal end of the dowel pin and drives it into the anchor, completing the tissue fixation. The length of the pin driver assembly is such that once the cap handle of the pin driver engages the proximal end of the pin insertion assembly, the pin is fully seated within the anchor. FIG. 9 shows the tissue anchor 2 of the present invention fully seated in bone, with dowel pin 18 inserted, thereby expanding slots 12, and securing tissue 32 against bone 34, with ridges 8 preventing the anchor from backing out of the bone.

Although the present invention has been described in relation to particular embodiments thereof, many other variations and modifications and other uses will become apparent to those skilled in the art.

What is claimed is:

1. A bioabsorbable expandable tissue anchor for sutureless fixation of soft tissue to bone, comprising:
   a cannulated shaft having a distal end and a proximal end, the shaft being divided into at least two longitudinal legs by longitudinal slots extending from the distal end of the shaft;
   a non-slotted severable distal region;
   a plurality of ribs formed on the cannulated shaft and extending at least partially circumferentially around the cannulated shaft;
   a dowel pin insertable in the proximal end of the cannulated shaft to axially spread apart the legs of the shaft by opening the longitudinal slots; and
   a cannulated head disposed on of the shaft.

2. The bioabsorbable expandable tissue anchor according to claim 1, wherein the head of the anchor has an oblong shape.

3. The bioabsorbable expandable tissue anchor according to claim 2, further comprising at least two barbs disposed on the head, at least one barb disposed at each longitudinal end of the oblong head, the barbs having respective pointed tips extending toward the distal end of the shaft for engaging the soft tissue upon insertion of the anchor into bone.

4. The bioabsorbable expandable tissue anchor according to claim 1, wherein the ribs have a truncated conical shape with a surface sloped at an angle with respect to the longitudinal axis of the tack, and the ribs have a major diameter greater than the diameter of the shaft of the tack.

5. The bioabsorbable expandable tissue anchor according to claim 1, wherein the slots are disposed on opposing sides of the shaft.

6. A method for sutureless fixation of tissue to bone using a bioabsorbable expandable tissue anchor having a cannulated shaft with a distal end, a proximal end, and longitudinal slots which extend from the distal end of the shaft and divide the shaft into at least two legs, a plurality of ribs formed on the cannulated shaft and extending at least partially circumferentially around the cannulated shaft, and a cannulated head disposed on the proximal end of the shaft, the method comprising:
   inserting a portion of an insertion assembly into the cannulation of the tissue anchor, the insertion assembly having a point which protrudes from the distal end of the anchor to penetrate the tissue and the bone;
   installing the bioabsorbable expandable tissue anchor through the tissue and into the bone;
   removing the insertion assembly from the cannulation of the tissue anchor; and
   inserting a dowel pin into the proximal end of the cannulated shaft to axially spread apart the legs of the shaft by opening the longitudinal slots.

7. The bioabsorbable expandable tissue anchor of claim 1, wherein said cannulated shaft has a cannula provided with a taper to define an opening at said distal end which is narrower than an opening at said proximal end.

8. The bioabsorbable expandable tissue anchor of claim 1, wherein pressure exerted by insertion of said dowel pin severs said non-slotted severable distal region.

9. The bioabsorbable expandable tissue anchor of claim 1, wherein the shaft is divided into two said longitudinal legs by two longitudinal slots.

10. A tissue anchoring device, comprising:
    a cannulated body including an axially expandable bone tissue engaging region formed of a plurality of flexible legs, said legs being joined at a proximal end of said body and separable at a severable connection at a distal end of said body; and
    a head including a plurality of arcurate slots and a soft tissue engaging region.

11. The tissue anchoring device of claim 10, further comprising an inner dowel pin insertable into the cannulated body, said dowel pin axially expanding said bone tissue engaging region upon insertion of the dowel pin into the cannulated body.

12. The tissue anchoring device of claim 10, wherein said device is bioabsorbable.

13. The tissue anchoring device of claim 10, wherein said arcurate slots are shaped to accept cleats of a driving device.

14. A tissue anchoring system, comprising:
    an expandable, bioabsorbable tissue anchor having a cannulation and comprising a head portion for receiving said driver and engaging tissue and a body portion with spreadable legs, said spreadable legs being separated by longitudinal slots and having ridges for engaging bone, said head portion having arcurate slots for receiving cleats of said driver and barbs for engaging said tissue;
    a driver;
    an insertion assembly having a portion insertable in the cannulation of said tissue anchor;
    a dowel pin; and
    a pin driver.

15. The tissue anchoring system of claim 14, wherein said driver comprises:
    cleats for engaging the arcurate slots in a head of said tissue anchor; and
    a cannula for receiving said insertion assembly.

* * * * *